(12) United States Patent
Zhang et al.

(10) Patent No.: US 10,773,078 B2
(45) Date of Patent: Sep. 15, 2020

(54) WIRE FIXING DEVICE FOR PACEMAKER ELECTRODE

(71) Applicant: Wuxi People's Hospital, Jiangsu (CN)

(72) Inventors: Changying Zhang, Jiangsu (CN); Shipeng Dang, Jiangsu (CN); Ruxing Wang, Jiangsu (CN); Zhiming Yu, Jiangsu (CN); Kulin Li, Jiangsu (CN); Jie Zheng, Jiangsu (CN); Xiaoyu Liu, Jiangsu (CN); Xiaoyan Li, Jiangsu (CN); Zhenye Zhang, Jiangsu (CN)

(73) Assignee: Wuxi People's Hospital, Jiangsu (CN)

( * ) Notice: Subject to any disclaimer, the term of this patent is extended or adjusted under 35 U.S.C. 154(b) by 252 days.

(21) Appl. No.: 15/920,481

(22) Filed: Mar. 14, 2018

(65) Prior Publication Data

US 2018/0264254 A1    Sep. 20, 2018

(30) Foreign Application Priority Data

Mar. 16, 2017  (CN) .......................... 2017 1 0156356

(51) Int. Cl.
*A61N 1/05* (2006.01)
(52) U.S. Cl.
CPC ................................... *A61N 1/059* (2013.01)

(58) Field of Classification Search
CPC .. A61N 1/059; A61N 1/0558; A61N 1/37518; A61N 1/057; A61N 2001/058
See application file for complete search history.

(56) References Cited

U.S. PATENT DOCUMENTS

| | | | | |
|---|---|---|---|---|
| 4,683,895 A | * | 8/1987 | Pohndorf | A61B 17/0644 248/505 |
| 2011/0288618 A1 | * | 11/2011 | Glen | A61N 1/0558 607/116 |

* cited by examiner

*Primary Examiner* — Tammie K Marlen
(74) *Attorney, Agent, or Firm* — JCIPRNET

(57) ABSTRACT

Provided is a wire fixing device for a cardiac pacemaker electrodes, including: an electrode fixator having an electrode clamping component, first hooks and second hooks; the electrode clamping component includes a first clamping piece and a second clamping piece that are semicircular cylindrical, the first clamping piece and the second clamping piece are connected by a clamp hinge connector, and a circular tube is formed when the electrode clamping component is closed; first hooks are provided on the back of the first clamping piece, second hooks are provided on the back of the second clamping piece, and hook tips of the first and second hooks are all bent towards a rotation direction of the electrode clamping component during closing; and the first and second hooks can be interlaced with each other when the electrode clamping component is closed, and can be separated when the electrode clamping component is open.

9 Claims, 1 Drawing Sheet

WIRE FIXING DEVICE FOR PACEMAKER ELECTRODE

CROSS-REFERENCE TO RELATED APPLICATION

This application claims the priority benefit of China application no. 201710156356.8, filed on Mar. 16, 2017. The entirety of the above-mentioned patent application is hereby incorporated by reference herein and made a part of this specification.

BACKGROUND

Technical Field of the Present Invention

The present invention relates to a wire fixing device for pacemaker electrode, belonging to the technical field of medical instruments.

Technical Background of the Present Invention

Currently, after implantation of a pacemaker and an electrode, the electrode is mainly fixed by using a suture. Fixing the electrode with a suture has the following disadvantages: 1. it is time and labor consuming; 2. the suture slips easily and the electrode may shift; 3. an excessively tight ligation may damage the electrode; 4. it is even more time and labor consuming to remove the suture and stitch again if the electrode needs to be moved.

SUMMARY OF THE INVENTION

An objective of the present invention is to overcome the defects in the prior art, and provide a wire fixing device for pacemaker electrode, which does not require a suture, achieves firm fixing, does not damage an electrode, and facilitates detachment and re-implantation.

According to the technical solution provided by the present invention, a wire fixing device for pacemaker electrode includes: an electrode fixator used for clamping the tail of an electrode, where the electrode fixator includes an electrode clamping component, first hooks and second hooks; the electrode clamping component includes a first clamping piece and a second clamping piece that are semicircular cylindrical, one side edge of the first clamping piece and one side edge of the second clamping piece are connected in a hinged manner by a clamp hinge connector, and a circular tube is formed when the electrode clamping component is closed; several first hooks are provided on the back of the first clamping piece, several second hooks are provided on the back of the second clamping piece, and hook tips of the first hooks and the second hooks are all bent towards a rotation direction of the electrode clamping component during closing; and the first hooks and the second hooks can be interlaced with each other when the electrode clamping component is closed, and can be separated when the electrode clamping component is open.

As a further improvement of the present invention, a plurality of circular ribs is provided on a peripheral surface at the tail of the electrode, a plurality of first semicircular grooves and second semicircular grooves are provided on inner walls of the first clamping piece and the second clamping piece respectively, and the first semicircular grooves and the second semicircular grooves can form circular grooves fitting the circular ribs when the electrode clamping component is closed.

As a further improvement of the present invention, first notches are provided at both ends of the other side edge of the first clamping piece respectively, second notches are provided at both ends of the other side edge of the second clamping piece respectively, and the first notches and the second notches are jointed when the electrode clamping component is closed, forming a threading hole for thread stitching and fixing.

As a further improvement of the present invention, the clamp hinge connector is an elastic hinge with two statuses, open and closed.

As a further improvement of the present invention, several first hooks are connected to the first clamping piece through a first hinge connector, and several second hooks are connected to the second clamping piece through a second hinge connector.

As a further improvement of the present invention, both the first hinge connector and the second hinge connector use elastic hinges.

As a further improvement of the present invention, a first block is provided on the back of the first hooks, a second block is provided on the back of the second hooks, all the first hooks are fixed with the first block, and all the second hooks are fixedly connected with the second block.

As a further improvement of the present invention, several first hooks and several second hooks are arranged in an interlaced manner along a length direction of the electrode clamping component.

As a further improvement of the present invention, a lug is provided on the other side edge of the first clamping piece, a bolt is provided on the other side edge of the second clamping piece, a plug hole for the bolt to plug in is provided on the lug, and the lug can be connected and locked with the bolt.

As a further improvement of the present invention, inner surfaces of each of the first clamping piece and the second clamping piece are provided with a soft lining layer.

As a further improvement of the present invention, the soft lining layer is made of a medical silicone material.

Compared with the prior art, the present invention has the following advantages: the present invention is ingenious in structure and reasonable in design. By means of fitting and connection between an electrode fixator and an electrode, the present invention does not require a suture but only requires two clipping actions, achieves film fixing, does not damage the electrode, and facilitates detachment and re-implantation.

Figure 1:
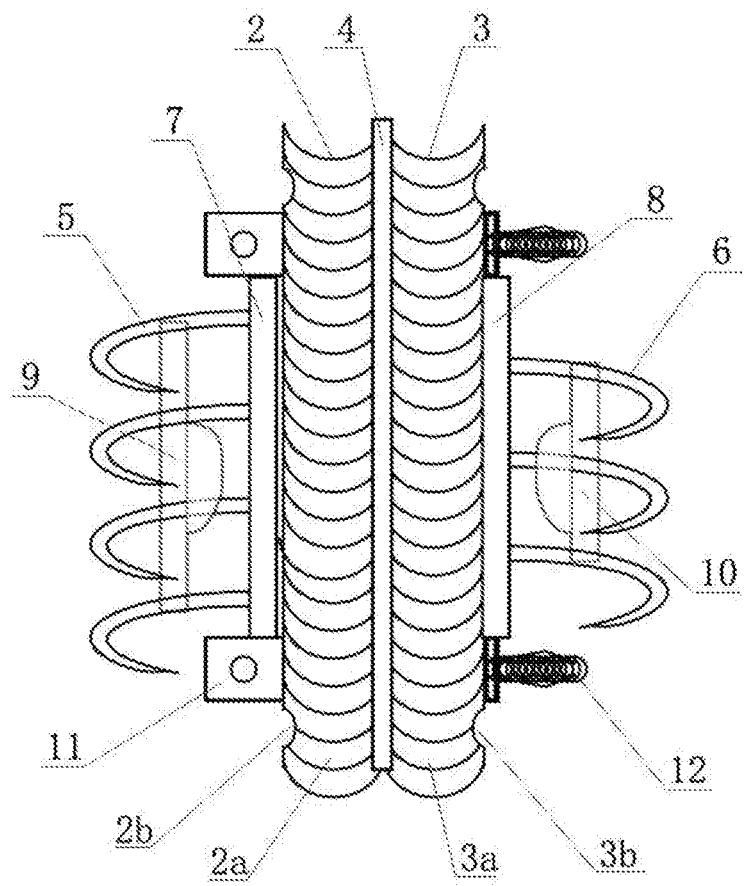
FIG. 1 is a schematic structural diagram of an electrode fixator in an embodiment of the present invention.

Meanings of reference numerals in the drawings: 1 represents an electrode, 1a represents a circular rib, 2 represents a first clamping piece, 2a represents a first semicircular groove, 2b represents a first notch, 3 represents a second clamping piece, 3a represents a second semicircular groove, 3b represents a second notch, 4 represents a clamp hinge connector, 5 represents a first hook, 6 represents a second hook, 7 represents a first hinge connector, 8 represents a second hinge connector, 9 represents a first block, 10 represents a second block, 11 represents a lug, and 12 represents a bolt.

DETAILED DESCRIPTION

The present invention is further described with reference to specific accompanying drawings and embodiments.

As shown in the figures, the wire fixing device for pacemaker electrode in the embodiment mainly includes two parts: an electrode 1 and an electrode fixator.

As shown in FIG. 1. the electrode fixator is used for clamping the tail of the electrode 1. The electrode fixator mainly includes an electrode clamping component, first hooks 5 and second hooks 6. The electrode clamping component includes a first clamping piece 2 and a second clamping piece 3 that are semicircular cylindrical, one side edge of the first clamping piece 2 and one side edge of the second clamping piece 3 are connected in a hinged manner by a clamp hinge connector 4, and a circular tube for clamping and being fixed at the tail of the electrode 1 is formed when the electrode clamping component is closed. Four first hooks 4 are provided on the back of the first clamping piece 2, three second hooks 6 are provided on the back of the second clamping piece 3, and hook tips of the first hooks 5 and the second hooks 6 are all bent towards a rotation direction of the electrode clamping component during closing. The first hooks 5 and the second hooks 6 can be interlaced with each other when the electrode clamping component is closed, and can be separated when the electrode clamping component is open.

In specific application, the electrode clamping component is opened first. Then, the tail of the electrode 1 is put between the first clamping piece 2 and the second clamping piece 3 of the electrode clamping component, the first clamping piece 2 and the second clamping piece 3 are shut, and the electrode clamping component is closed to clamp and fix the electrode 1. The first hooks 5 and the second hooks 6 are turned to be interlaced, so as to hook tissues. As such, the pacemaker electrode 1 is fixed quickly.

Figure 2:
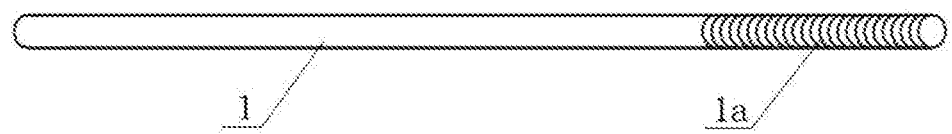
FIG. 2 is a schematic structural diagram of an electrode in an embodiment of the present invention.

As shown in FIG. 1 and FIG. 2, in this embodiment, a plurality of circular ribs 1a is provided on a peripheral surface at the tail of the electrode 1. Several first semicircular grooves 2a and second semicircular grooves 3a are provided on inner walls of the first clamping piece 2 and the second clamping piece 3 respectively. The first semicircular grooves 2a and the second semicircular grooves 3a can form circular grooves fitting the circular ribs 1a when the electrode clamping component is closed. In specific use, the fitting between the *circulars* rib 1a and the circular grooves enables the electrode fixator to stably and thinly clamp and fix the electrode 1 directly.

As shown in FIG. 1, in this embodiment, first notches 2b are provided at both ends of the other side edge of the first clamping piece 2 respectively, second notches 3b are provided at both ends of the other side edge of the second clamping piece 3 respectively, and the first notches 2b and the second notches 3b are jointed when the electrode clamping component is closed, forming a threading hole for thread stitching and fixing. As such, in addition to fixing based on the first hooks 5 and the second hooks 6, a suture can still be used for fixing in the present invention.

As shown in FIG. 1, in this embodiment, the clamp hinge connector 4 uses an elastic hinge. Four first hooks 5 are connected to the first clamping piece 2 through a first hinge connector 7, and three second hooks 6 are connected to the second clamping piece 3 through a second hinge connector 8. Both the first hinge connector 7 and the second hinge connector 8 use elastic hinges. The elastic hinge has two states: an open state and a closed state. That is, when turned to one position, the elastic hinge is maintained in an open state, and when turned to another position, the elastic hinge is maintained in a closed state. Such a design can facilitate installation and detachment of the electrode fixator.

As shown in FIG. 1, in this embodiment, a first block 9 is provided on the back of the first hooks 5, and a second block 10 is provided on the back of the second hooks 6. As such, the first hooks 5 and the second hooks 6 can be turned conveniently, facilitating installation and detachment of the electrode fixator. In this embodiment, the four first hooks 5 are all fixedly connected with the first block 9, and the three second hooks 6 are all fixedly connected with the second block 10, so that the first hooks 5 and the second hooks 6 have higher structural strength and are safer and more reliable.

As shown in FIG. 1, in this embodiment, four first hooks 5 and three second hooks 6 are arranged in an interlaced manner along a length direction of the electrode clamping component, so as to better hook tissues and ensure the fixing effect.

As shown in FIG. 1, in this embodiment, a lug 11 is provided on the other side edge of the first clamping piece 2, a bolt 12 is provided on the other side edge of the second clamping piece 3, a plug hole for the bolt 12 to plug in is provided on the lug 11, and the lug 11 can be connected and locked with the bolt 12. As such, it can be ensured that the electrode fixator is safer after being closed, preventing the electrode 1 from being disengaged due to opening of the electrode fixator under an accidental external force. Definitely, the fitting between the lug 11 and the bolt 12 may be replaced with another collection and locking structure, and such a regular replacement should still belong to the protection scope of the present invention.

As shown in FIG. 1, in this embodiment, inner surfaces of the first clamping piece 2 and the second clamping piece 3 are each provided with a soft lining layer. The soft lining layer can protect the electrode 1. The soft lining layer is preferably made of a medical silicone material.

What is claimed is:

1. A wire fixing device for pacemaker electrodes, comprising an electrode fixator configured for clamping a tail of an electrode, wherein the electrode fixator comprises an electrode clamping component, first hooks and second hooks; the electrode clamping component comprises a first clamping piece and a second clamping piece that are semicircular cylindrical, one side edge of the first clamping piece and one side edge of the second clamping piece are connected in a hinged manner by a clamp hinge connector, and a circular tube is formed when the electrode clamping component is closed; the first hooks are provided on a back of the first clamping piece, the second hooks are provided on a back of the second clamping piece, and hook tips of the first hooks and hook tips of the second hooks are all bent towards a rotation direction of the electrode clamping component during closing; and the first hooks and the second hooks are capable of being interlaced with each other when the electrode clamping component is closed, and are capable of being separated with each other when the electrode clamping component is open; and wherein a lug is provided on another side edge of the first clamping piece, a bolt is provided on another side edge of the second clamping piece, a plug hole for the bolt to plug in is provided on the lug, and the lug is capable of being connected and locked with the bolt.

2. The wire fixing device according to claim 1, wherein a plurality of first semicircular grooves and a plurality of second semicircular grooves are provided on inner wall of the first clamping piece and inner wall of the second clamping piece respectively, and the first semicircular grooves and the second semicircular grooves are configured for fitting circular ribs provided on a peripheral surface at the tail of the electrode when the electrode clamping component is closed.

3. The wire fixing device according to claim 1, wherein a first notch is provided at each ends of another side edge of the first clamping piece, a second notch is provided at each ends of another side edge of the second clamping piece, and the first notches and the second notches are configured to be combined to form threading holes when the electrode clamping component is closed.

4. The wire fixing device according to claim 1, wherein the clamp hinge connector is an elastic hinge with two statuses, open and closed.

5. The wire fixing device according to claim 1, wherein the first hooks are connected to the first clamping piece through a first hinge connector, and the second hooks are connected to the second clamping piece through a second hinge connector.

6. The wire fixing device according to claim 5, wherein both the first hinge connector and the second hinge connector are elastic hinges.

7. The wire fixing device according to claim 1, wherein a first block is provided on the first hooks, a second block is provided on the second hooks, all the first hooks are fixed with the first block, and all the second hooks are fixedly connected with the second block.

8. The wire fixing device according to claim 1, wherein the first hooks and the second hooks are arranged in an interlaced manner along a length direction of the electrode clamping component.

9. The wire fixing device according to claim 1, wherein inner surfaces of each of the first clamping piece and the second clamping piece are provided with a lining layer with medical silicone material.

* * * * *